(12) United States Patent
Kondo et al.

(10) Patent No.: US 11,419,820 B2
(45) Date of Patent: Aug. 23, 2022

(54) CAROTENOID-CONTAINING PARTICLES

(71) Applicant: Riken Vitamin Co., Ltd., Tokyo (JP)

(72) Inventors: Kazuyoshi Kondo, Tokyo (JP); Isao Matsuse, Tokyo (JP)

(73) Assignee: Riken Vitamin Co., Ltd., Tokyo (JP)

( * ) Notice: Subject to any disclaimer, the term of this patent is extended or adjusted under 35 U.S.C. 154(b) by 321 days.

(21) Appl. No.: 16/088,303

(22) PCT Filed: Mar. 28, 2017

(86) PCT No.: PCT/JP2017/012601
§ 371 (c)(1),
(2) Date: Sep. 25, 2018

(87) PCT Pub. No.: WO2017/170528
PCT Pub. Date: Oct. 5, 2017

(65) Prior Publication Data
US 2020/0297637 A1 Sep. 24, 2020

(30) Foreign Application Priority Data

Mar. 30, 2016 (JP) .............................. JP2016-068339

(51) Int. Cl.
| | |
|---|---|
| *A61K 9/16* | (2006.01) |
| *A23L 33/17* | (2016.01) |
| *A23L 33/105* | (2016.01) |
| *A23L 33/15* | (2016.01) |
| *A61K 31/015* | (2006.01) |
| *A61K 31/047* | (2006.01) |
| *A61K 31/122* | (2006.01) |
| *A61K 9/107* | (2006.01) |
| *A61K 45/06* | (2006.01) |

(52) U.S. Cl.
CPC .......... *A61K 9/1658* (2013.01); *A23L 33/105* (2016.08); *A23L 33/15* (2016.08); *A23L 33/17* (2016.08); *A61K 9/1611* (2013.01); *A61K 9/1652* (2013.01); *A61K 31/015* (2013.01); *A61K 31/047* (2013.01); *A61K 31/122* (2013.01); *A61K 9/107* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 5,961,990 | A * | 10/1999 | Delrieu | A61Q 17/04 424/401 |
| 6,203,804 | B1 * | 3/2001 | Murakado | A61K 8/73 424/401 |
| 6,391,288 | B1 | 5/2002 | Miyazawa et al. | |
| 6,979,467 | B1 | 12/2005 | Garces Garces et al. | |
| 2002/0052421 | A1 | 5/2002 | Sadano et al. | |
| 2003/0059462 | A1 * | 3/2003 | Barenholz | A61K 8/14 424/450 |
| 2003/0104080 | A1 * | 6/2003 | Singh | A61K 8/678 424/729 |
| 2007/0036868 | A1 * | 2/2007 | Chiavazza | A23L 33/185 424/489 |
| 2009/0263473 | A1 * | 10/2009 | Hong | A61P 29/00 424/450 |
| 2009/0274757 | A1 * | 11/2009 | Clark | A61K 31/565 424/476 |
| 2010/0305227 | A1 * | 12/2010 | Parker | C08G 18/0838 435/68.1 |
| 2011/0236446 | A1 * | 9/2011 | Takagi | A61K 8/04 424/59 |

FOREIGN PATENT DOCUMENTS

| | | |
|---|---|---|
| EP | 0 285 682 A1 | 10/1988 |
| JP | 60-251864 A | 12/1985 |
| JP | 05-316995 A | 12/1993 |
| JP | H0625156 A | 2/1994 |
| JP | 07-289200 A | 11/1995 |
| JP | 2001-96146 A | 4/2001 |
| JP | 2001-524123 A | 11/2001 |
| JP | 2002-129057 A | 5/2002 |
| JP | 2003-523316 A | 8/2003 |
| JP | 2006-109792 A | 4/2006 |
| JP | 2013-034446 A | 2/2013 |
| WO | WO9513047 * | 5/1995 |
| WO | WO 98/50000 A2 | 11/1998 |
| WO | WO 01/47560 A2 | 7/2001 |

OTHER PUBLICATIONS

Miyazawa et al., Preparation of a new soft capsule for cosmetics, ]. Cosmet. Sci.J 51, 239-252 Jul./Aug. 2000) (Year: 2000).*
Cosmetics and Toiletries., Croda Sources Pea Superfood for Hair and Skin Ingredients, https://www.cosmeticsandtoiletries.com/formulating/function/moisturizer/Croda-Sources-Pea-Superfood-for-Hair-and-Skin-Ingredients-270157051.html., Aug. 6, 2014 (Year: 2014).*
Rungruangmaitree et al., Pea, *Pisum sativum*, and its anticancer activity. Pharmacogon Rev. Jan.-Jun. 2017; 11(21): 39-42 (Year: 2017).*
International Preliminary Report on Patentability for PCT/JP2017/012601 dated Oct. 11, 2018.
Supplementary European Search Report for EP 17775065 dated Oct. 15, 2019.

(Continued)

*Primary Examiner* — Jennifer A Berrios
(74) *Attorney, Agent, or Firm* — Knobbe, Martens, Olson & Bear, LLP

(57) ABSTRACT

Provided are carotenoid-containing particles having, for preventing exudation of carotenoid at the time of tableting and during storage, a structure in which a carotenoid is dispersed in an agar gel containing a cyclodextrin and/or a plant protein.

19 Claims, 11 Drawing Sheets

(56) References Cited

OTHER PUBLICATIONS

International Search Report for PCT/JP2017/012601 dated Jun. 27, 2017.
Indian Examination Report for Indian Application No. 201827032606 dated Jun. 15, 2021.
Blanco-Fernandez, Barbara et al., "Synergistic performance of cyclodextrin-agar hydrogels for ciprofloxacin delivery and antimicrobial effect" Carbohydrate Polymers, 2011, pp. 765-774, vol. 85.
Moriguchi, Natsumi et al., "Formation of Bicontinuous Phase on Egg White Protein/agar Co-gels and their Fracture Properties" Nippon Shokuhin Kagaku Kogaku Kaishi, 2013, pp. 225-232, vol. 60, No. 5.

\* cited by examiner

CAROTENOID-CONTAINING PARTICLES

CROSS REFERENCE TO RELATED APPLICATIONS

This application is a U.S. National Phase Application of PCT International Application Number PCT/JP2017/012601, filed on Mar. 28, 2017, designating the United States of America and published in the Japanese language, which is an International Application of and claims the benefit of priority to Japanese Patent Application No. 2016-068339, filed on Mar. 30, 2016. The disclosures of the above-referenced applications are hereby expressly incorporated by reference in their entireties.

TECHNICAL FIELD

The present invention relates to particles containing carotenoids.

BACKGROUND ART

Carotenoids, which are oil-soluble pigments being yellow to red or the like in color and having a long chain of conjugated double bonds, have conventionally been used as colorants for foods. In addition, carotenoids have been found to exhibit various kinds of physiological activities, such as a provitamin A activity, i.e., being convertible into vitamin A in vivo, an antioxidant action, and an anticancer/antitumor action, and therefore, have attracted increasing attention as active ingredients of drugs, health foods, or the like.

For use in a drug, health food, etc., a carotenoid is generally made into particles, blended with another active ingredient, an excipient, etc. by powder mixing, and then compressed into tablets. Example of the method for producing carotenoid-containing particles include a method in which the carotenoid is dispersed in an aqueous solution consisting mainly of a hydrophilic polymer gelator capable of thermoreversible sol-gel transition, the dispersion is granulated, and the granules are dried. In this method, the hydrophilic polymer gel as the continuous phase forms a coating that protects the carotenoid as the dispersed phase, thus providing an appropriate strength to the particles. Therefore, the particles obtainable by this method are suitable for tablet compression. In particular, particles obtained by using gelatin as the hydrophilic polymer gelator have a high strength and an excellent barrier performance (ability to block external heat, light, and air and to retain the included carotenoid, i.e., to prevent it from exuding), and for the reason, are preferably used.

On the other hand, gelatin, which is an animal protein, has a risk of inducing allergy. Therefore, in recent years, there has been an increasing need of substituting gelatin with other ingredients having a lower risk of allergy induction, in the fields of drugs, health foods, etc. However, in the cases where a hydrophilic polymer gelator other than gelatin (agar, carrageenan, alginic acid, etc.) is used in the method for producing carotenoid-containing particles, carotenoid may sometimes be exuded from the particles due to the pressure applied at the time of tableting or due to external factors (heat, impact, etc.) of storage.

Generally, in order to prevent the exudation of carotenoid from carotenoid-containing particles at the time of tableting and/or during storage, adjusting the carotenoid content in the particles to a lower level is known to be effective. However, such a reduced carotenoid content in the particles is not favorable because it becomes necessary to take a large amount of the particles to obtain the efficacy of the carotenoid. As a method for preventing the exudation of carotenoid not by adjusting the carotenoid content, a method in which a carotenoid is dissolved or dispersed in a medium-chain triglyceride beforehand to form the dispersed phase (Patent Literature 1) has been proposed, for example. However, even when this method is applied to the production of carotenoid-containing particles using a hydrophilic polymer gelator other than gelatin, it is difficult to sufficiently prevent the exudation of carotenoid from the particles.

In these circumstances, a method for sufficiently preventing the exudation of carotenoid at the time of tableting and during storage not using gelatin as a hydrophilic polymer gelator has been sought for.

CITATION LIST

Patent Literature

Patent Literature 1: JP 2002-129057 A

SUMMARY OF INVENTION

Technical Problem

An object of the present invention is to provide carotenoid-containing particles from which the exudation of carotenoid at the time of tableting and during storage is prevented.

Solution to Problem

The present inventors made extensive examination to solve the problem described above. As a result, the inventors found that carotenoid-containing particles produced by a method characterized by using agar as a hydrophilic polymer gelator to constitute the continuous phase and adding a cyclodextrin and/or a plant protein to the agar are less likely to allow the carotenoid to exude from the particles, and based on the fact, completed the present invention.

That is, the present invention includes the following (1) and (2).

(1) Carotenoid-containing particles having a structure in which a carotenoid is dispersed in an agar gel containing a cyclodextrin and/or a plant protein.

(2) A method for producing carotenoid-containing particles, the method comprising the steps of preparing an oil-in-water emulsion composition by dispersing an oily phase containing a carotenoid in an aqueous phase containing agar and a cyclodextrin and/or a plant protein; and subsequently allowing the oil-in-water emulsion composition to form droplets and cooling the droplets for solidification.

Advantageous Effects of Invention

The carotenoid-containing particles of the present invention are characterized in that the exudation of carotenoid at the time of tableting and during storage is prevented.

The carotenoid-containing particles of the present invention are characterized in that, even when the carotenoid content in the particles is increased, exudation of carotenoid is less likely to occur.

The carotenoid-containing particles of the present invention are characterized in that, since no material of animal origin, such as gelatin, is contained as an essential compo-

DESCRIPTION OF EMBODIMENTS

Figure 1:
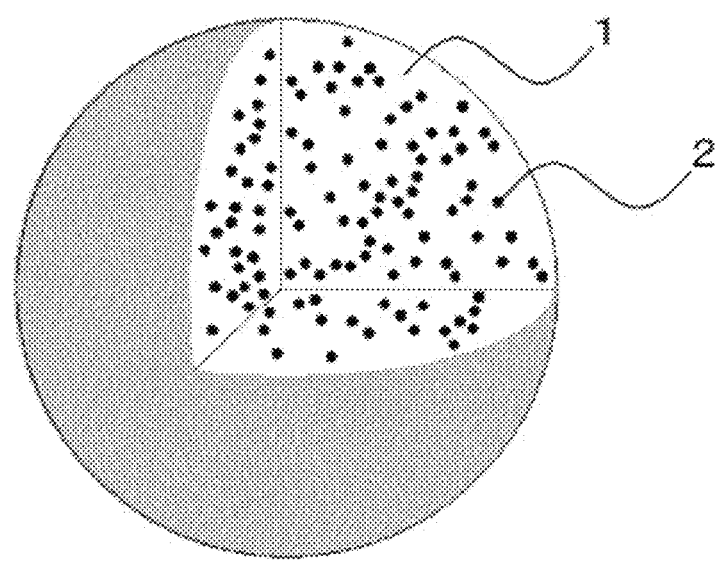
FIG. 1 is a schematic diagram showing the structure of a carotenoid-containing particle of the present invention.
Figure 2:
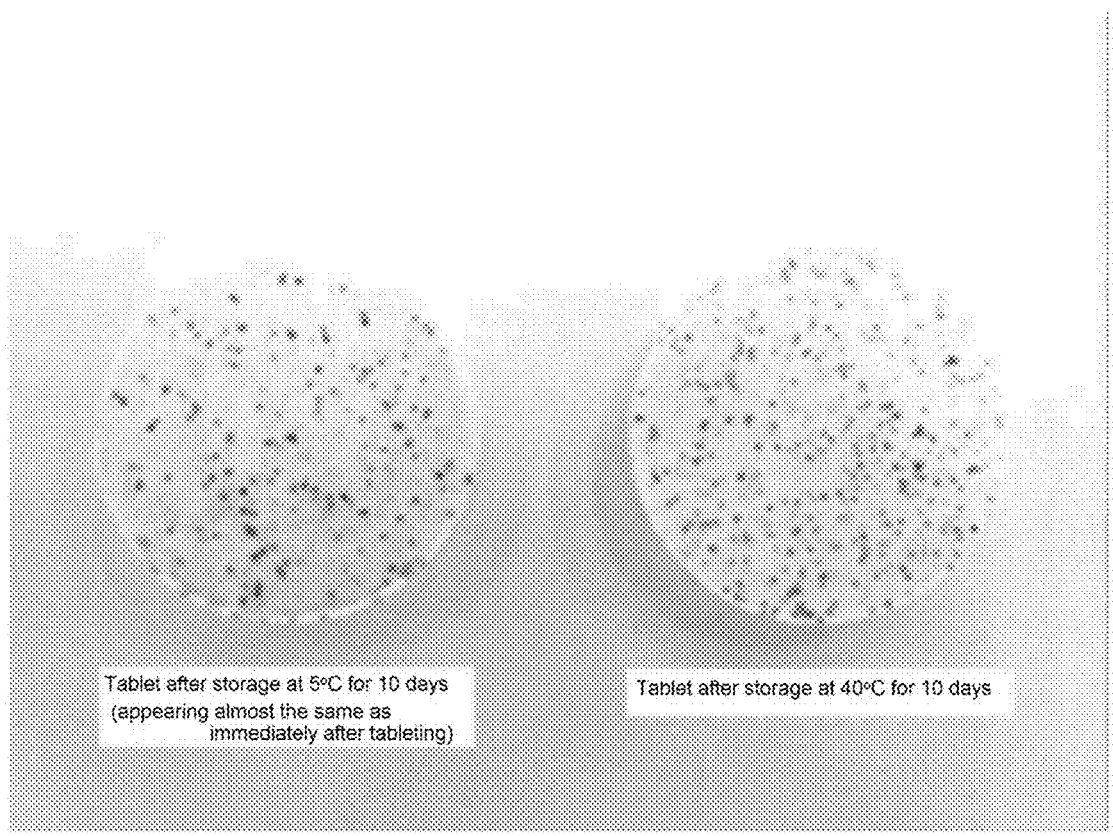
FIG. 2 shows a photograph of Tablet 1 produced in "Evaluation test of exudation of carotenoid due to tableting". In this photograph, one tablet stored at 5° C. for 10 days after tableting and one tablet stored at 40° C. for 10 days after tableting are placed side by side.
Figure 3:
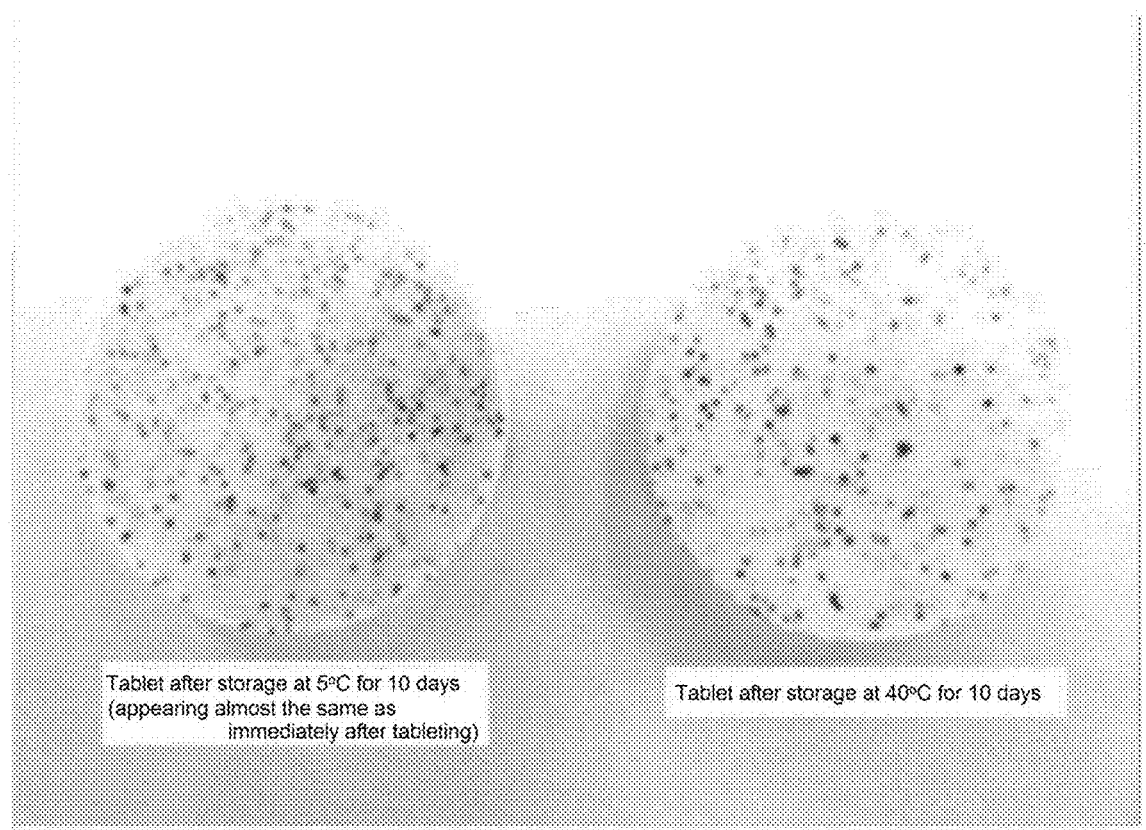
FIG. 3 shows a photograph of Tablet 2 produced in "Evaluation test of exudation of carotenoid due to tableting". In this photograph, one tablet stored at 5° C. for 10 days after tableting and one tablet stored at 40° C. for 10 days after tableting are placed side by side.
Figure 4:
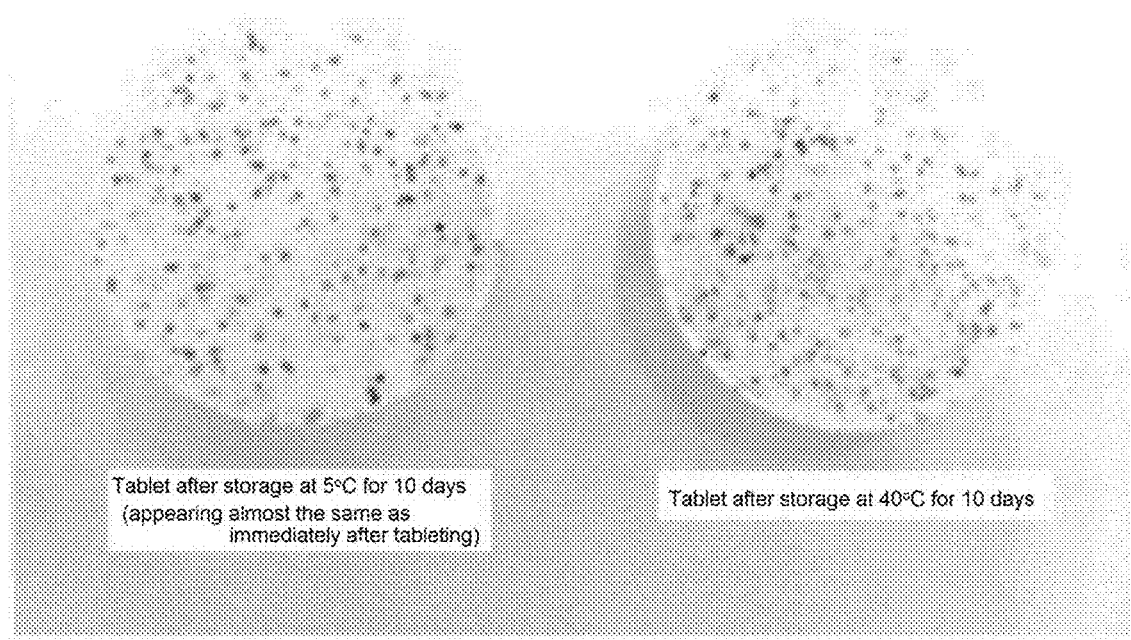
FIG. 4 shows a photograph of Tablet 3 produced in "Evaluation test of exudation of carotenoid due to tableting". In this photograph, one tablet stored at 5° C. for 10 days after tableting and one tablet stored at 40° C. for 10 days after tableting are placed side by side.
Figure 5:
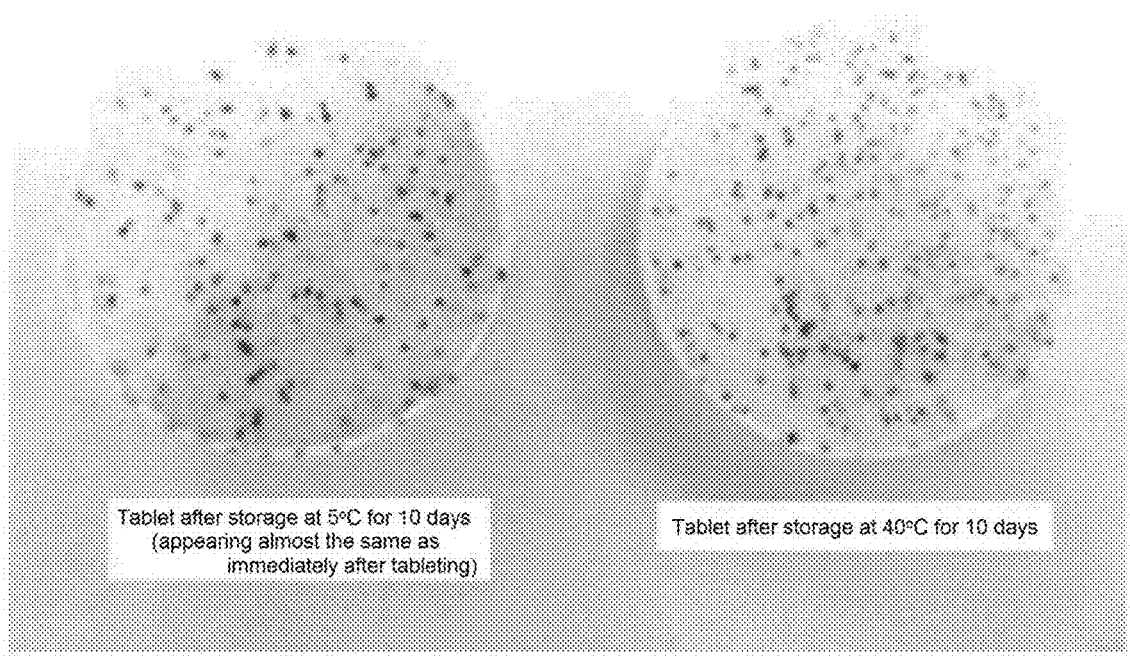
FIG. 5 shows a photograph of Tablet 4 produced in "Evaluation test of exudation of carotenoid due to tableting". In this photograph, one tablet stored at 5° C. for 10 days after tableting and one tablet stored at 40° C. for 10 days after tableting are placed side by side.
Figure 6:
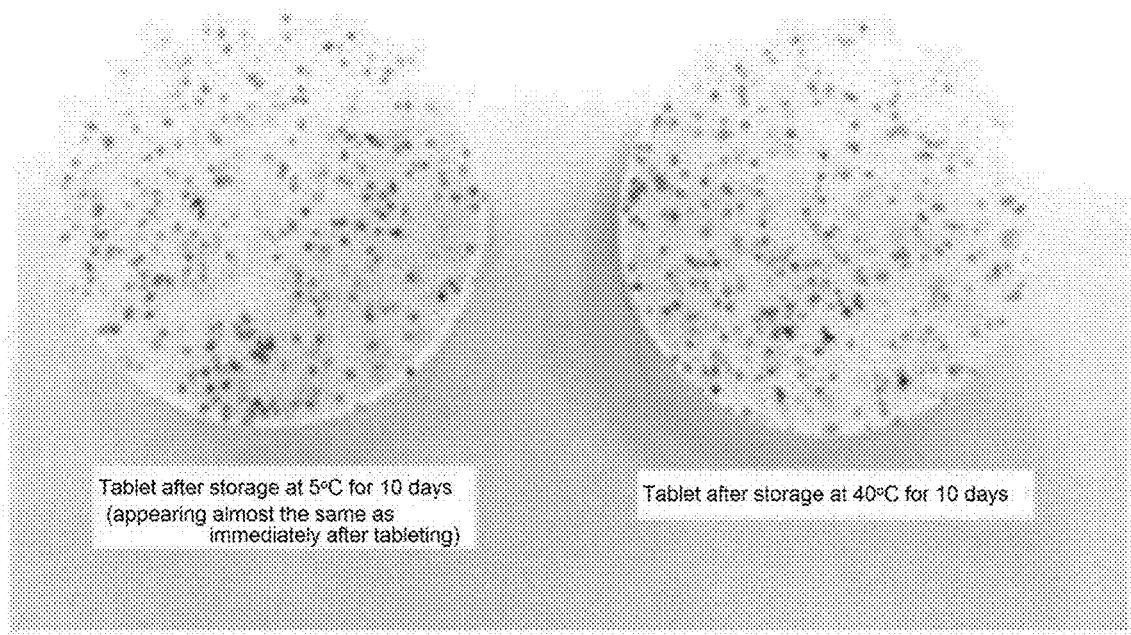
FIG. 6 shows a photograph of Tablet 5 produced in "Evaluation test of exudation of carotenoid due to tableting". In this photograph, one tablet stored at 5° C. for 10 days after tableting and one tablet stored at 40° C. for 10 days after tableting are placed side by side.
Figure 7:
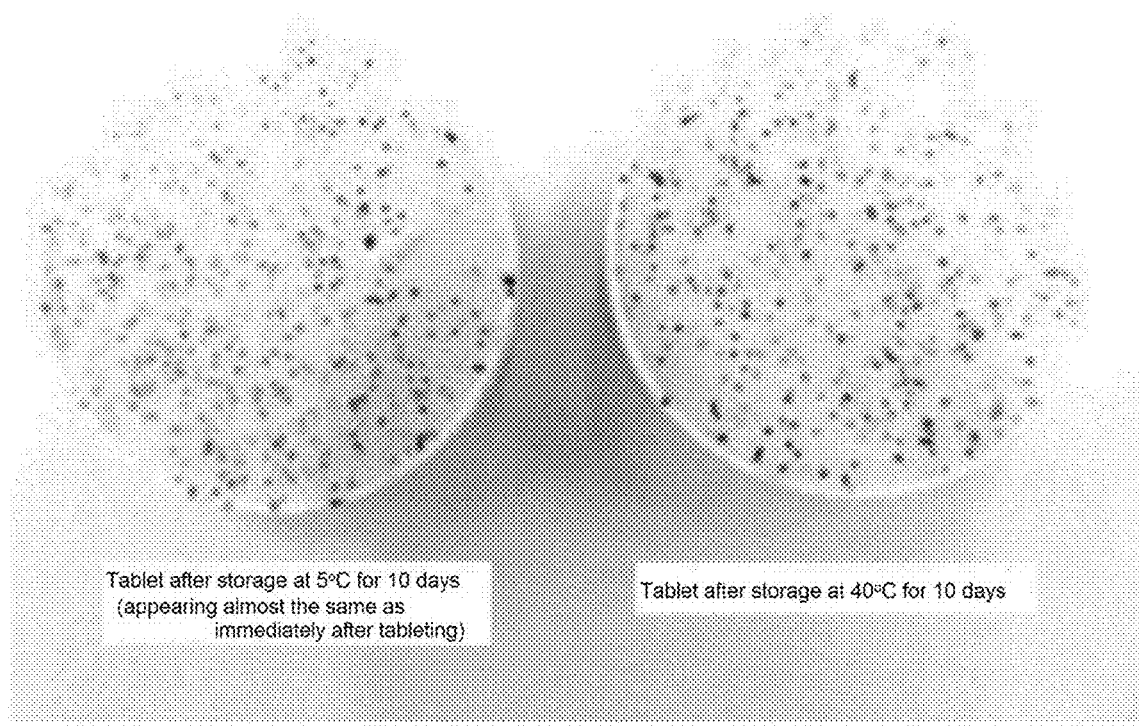
FIG. 7 shows a photograph of Tablet 6 produced in "Evaluation test of exudation of carotenoid due to tableting". In this photograph, one tablet stored at 5° C. for 10 days after tableting and one tablet stored at 40° C. for 10 days after tableting are placed side by side.
Figure 8:
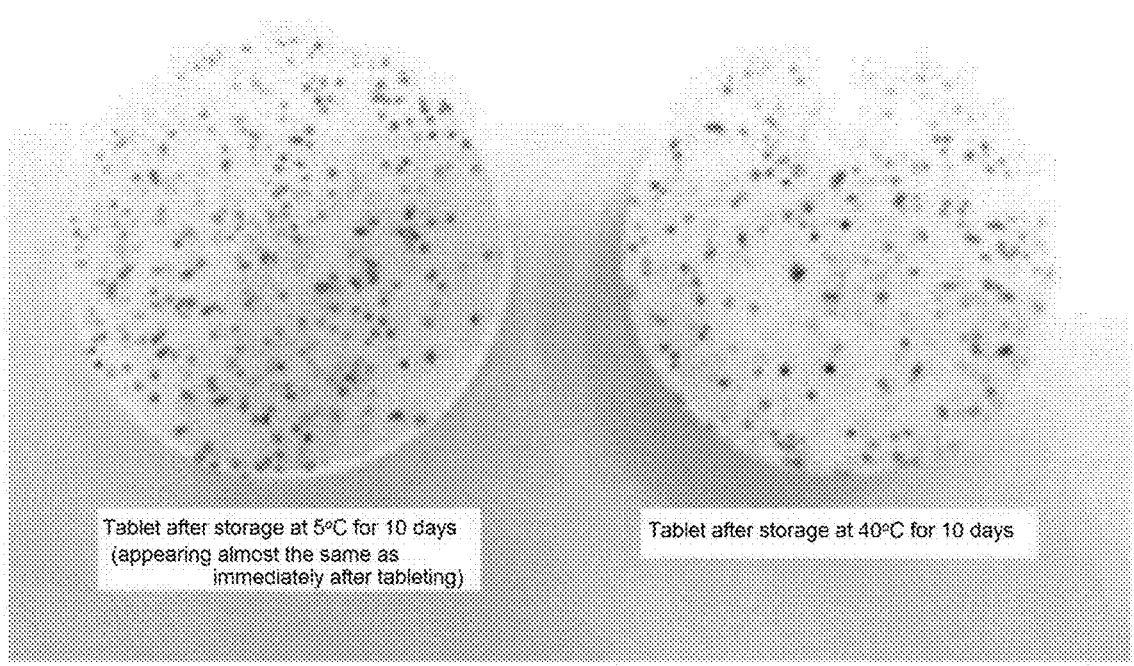
FIG. 8 shows a photograph of Tablet 7 produced in "Evaluation test of exudation of carotenoid due to tableting". In this photograph, one tablet stored at 5° C. for 10 days after tableting and one tablet stored at 40° C. for 10 days after tableting are placed side by side.
Figure 9:
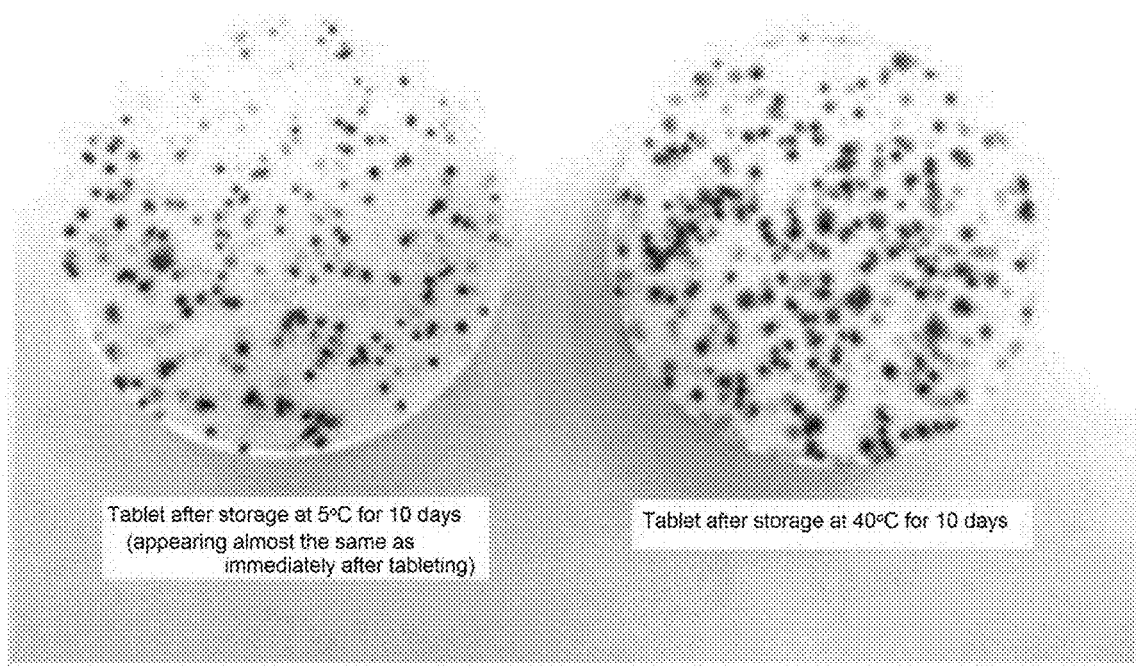
FIG. 9 shows a photograph of Tablet 8 produced in "Evaluation test of exudation of carotenoid due to tableting". In this photograph, one tablet stored at 5° C. for 10 days after tableting and one tablet stored at 40° C. for 10 days after tableting are placed side by side.
Figure 10:
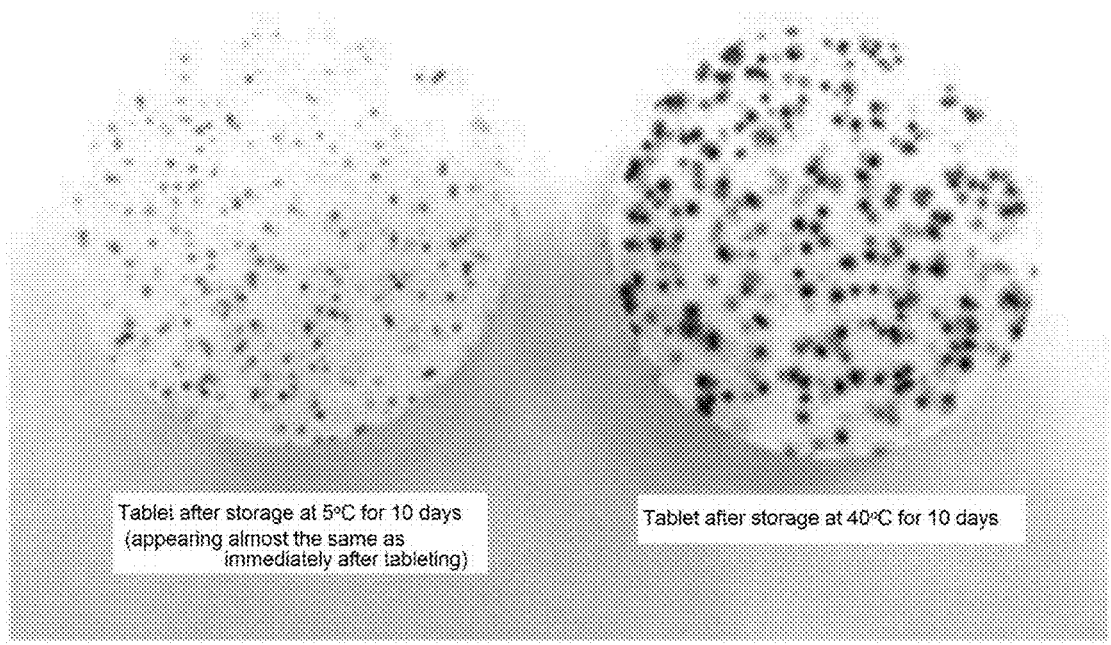
FIG. 10 shows a photograph of Tablet 9 produced in "Evaluation test of exudation of carotenoid due to tableting". In this photograph, one tablet stored at 5° C. for 10 days after tableting and one tablet stored at 40° C. for 10 days after tableting are placed side by side.
Figure 11:
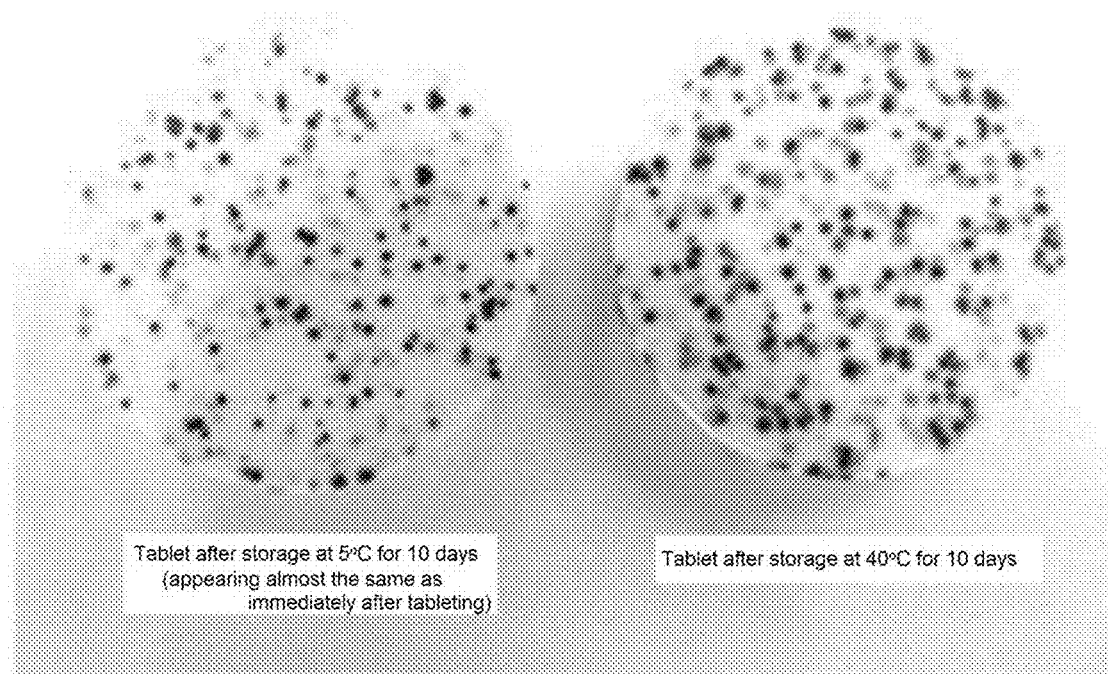
FIG. 11 shows a photograph of Tablet 10 produced in "Evaluation test of exudation of carotenoid due to tableting". In this photograph, one tablet stored at 5° C. for 10 days after tableting and one tablet stored at 40° C. for 10 days after tableting are placed side by side.

The carotenoid-containing particles of the present invention are characterized in that the particles have a structure in which a carotenoid is dispersed in an agar gel containing a cyclodextrin and/or a plant protein. In the carotenoid-containing particles of the present invention, for example, an agar gel containing a cyclodextrin and/or a plant protein may constitute an aqueous continuous phase, and a carotenoid may constitute an oily dispersed phase (see FIG. 1).

The agar gel constituting the continuous phase of the carotenoid-containing particles of the present invention is preferably one obtained by gelation of an agar as a hydrophilic polymer gelator capable of thermoreversible sol-gel transition. The agar is not particularly limited, but preferred is one extracted from red algae, such as *Gelidium, Gracilaria, Pterocladiella*, and *Ahnfeltia*. The form of the agar may be agar powder, agar flake, agar stick, agar thread, or the like, but agar powder is preferably used because it is highly soluble and easy to handle.

The molecular weight of the agar is not particularly limited, and usually those having a weight average molecular weight of 50000 to 60000 may be used. The weight average molecular weight is determined by gel filtration chromatography.

The jelly strength of the agar is not particularly limited, and for example, those having a jelly strength of 250 to 350 $g/cm^2$ are preferably used. The jelly strength is a value measured by the Nikkansui method (a method used in Japan Agar Marine Industry Union). That is, the jelly strength is determined by preparing a 1.5% by mass aqueous solution of agar, leaving it at 20° C. for 15 hours for gelation, and then measuring the maximum load per $cm^2$ applied to the surface of the obtained gel without causing collapse of the jelly for 20 seconds.

As an agar, for example, Ina Agar UP-37 (trade name; powder agar; made by Ina Food Industry) is commercially manufactured and marketed, and this agar may be used in the present invention.

The continuous phase of the carotenoid-containing particles of the present invention can be obtained by, for example, adding a cyclodextrin and/or a plant protein to the agar gel. In particular, using both of them in combination is preferable because more marked effect of the present invention is achieved, i.e., the exudation of carotenoid can be prevented for a longer period of time.

The cyclodextrin used in the present invention is a kind of cyclic oligosaccharide made of several D-glucose molecules bound together through α-(1→4) glucoside linkages to form a ring, and examples thereof include α-cyclodextrin (6 glucose molecules are bound), β-cyclodextrin (7 glucose molecules are bound), γ-cyclodextrin (8 glucose molecules are bound), etc. Of them, β-cyclodextrin and γ-cyclodextrin are preferred, and in particular, γ-cyclodextrin is preferred. One kind of these cyclodextrins may be used alone, and also two or more kinds thereof may be used in any combination.

As a cyclodextrin, for example, Dexy pearl α-100 (trade name; α-cyclodextrin; made by Ensuiko Sugar Refining Co., Ltd.), Dexy pearl β-100 (trade name; β-cyclodextrin; made by Ensuiko Sugar Refining Co., Ltd.), Dexy pearl γ-100 (trade name; γ-cyclodextrin; made by Ensuiko Sugar Refining Co., Ltd.), etc. are commercially manufactured and marketed, and these may be used in the present invention.

The plant protein used in the present invention is not particularly limited as long as it is a protein of edible plant origin, and examples thereof include soybean protein, wheat protein, rice protein, green-pea protein, corn protein, etc. One kind of these proteins may be used alone, and also two or more kinds thereof may be used in any combination.

As a plant protein, for example, Fujipro FX (trade name; soy protein; made by Fuji Oil Co., Ltd.), Protein GP (trade name; green pea protein; made by Daiichi Kasei Co., Ltd.), Oryza Protein-P70 (trade name; rice protein; made by Oryza Oil & Fat Chemical Co., Ltd.), etc. are commercially manufactured and marketed, and these may be used in the present invention.

To the continuous phase of the carotenoid-containing particles of the present invention, it is preferable to add a silicate in addition to the cyclodextrin and/or the plant protein. The addition of a silicate results in more marked effect of the present invention, i.e., even when the carotenoid content in the particles is increased, exudation of carotenoid is less likely to occur.

Examples of the silicate include alkaline earth metal silicates, such as calcium silicate, magnesium silicate (including magnesium trisilicate etc.), aluminium silicate, calcium aluminium silicate, calcium magnesium silicate (including calcium magnesium orthosilicate etc.), and aluminum magnesium silicate. Preferred are calcium silicate and magnesium silicate, and more preferred is calcium silicate. As a calcium silicate, for example, Florite R (trade name; made by Tomita Pharmaceutical Co., Ltd.) is commercially manufactured and marketed, and this calcium silicate may be used in the present invention.

The carotenoid constituting the dispersed phase of the carotenoid-containing particles of the present invention is an oil-soluble pigment being yellow to red or the like in color and having a long chain of conjugated double bonds, and specific examples thereof include β-carotene, α-carotene, γ-carotene, β-apo-8'-carotenal, β-apo-10'-carotenal, β-apo-8'-carotenic acid, citranaxanthin, lycopene, zeaxanthin, cryptoxanthin, echinenone, 3-hydroxy-β-carotene, fucoxanthin, lutein, astaxanthin, canthaxanthin, capsanthin, capsorubin, bixin, crocetin, and esters of a hydroxyl- or carboxyl-group-containing compound thereof, etc. Of them, preferred for use in the present invention are astaxanthin, lutein, and β-carotene, which are often blended in drugs, health foods, etc. The present invention is particularly excellent in that the effect of the present invention is sufficiently achieved even when astaxanthin, which tends to cause problems regarding oil exudation, is used. The carotenoids may be ones obtained by extraction from an animal or plant and subsequent purification, or by fermentation or synthesis. However, to reduce the risk of inducing allergy attributable to a material of animal origin, it is preferred not to use carotenoids of animal origin. Examples of carotenoid-containing natural pigments include annatto pigment, sweet potato carotene, shrimp pigment, krill pigment, orange pigment, crab pigment, Dunaliella carotene, capsicum pigment (paprika pigment), corn pigment, tomato pigment, carrot carotene, palm oil carotene, Phaffia pigment, powdered annatto, Haematococcus algae pigment, marigold pigment, etc.

In the present invention, as an index of the color, yellow to red, or the like, the Munsell hue circle may be used, for example.

For oxidation prevention and viscosity control, carotenoids are generally distributed in the form of carotenoid-containing oils in which carotenoids are dissolved or dispersed in oils. The carotenoid used in the present invention may be in the form of such a carotenoid-containing oil. In this case, the oil as the dispersion medium for the carotenoids is not particularly limited as long as it is an edible oil. However, to reduce the risk of inducing allergy attributable to a material of animal origin, it is preferred not to use oils of animal origin.

As a carotenoid, for example, AstaReal Oil 50F (trade name; oil containing 5% by mass astaxanthin; made by Fuji Chemical Industries Co., Ltd.), FloraGLO Lutein 20% suspension SAF (trade name; oil containing 20% by mass lutein; made by DSM), Lucarotin 30M (trade name; oil containing 30% by mass β-caroten; made by BASF), etc. are commercially manufactured and marketed, and these may be used in the present invention.

The method for producing the carotenoid-containing particles of the present invention is not particularly limited, but preferred is a method to give particles having a structure in which a carotenoid is dispersed in the continuous phase. Specific examples of such a method include a method comprising the steps of preparing an oil-in-water emulsion composition by dispersing an oily phase containing a carotenoid in an aqueous phase containing agar and a cyclodextrin and/or a plant protein; and subsequently allowing the oil-in-water emulsion composition to form droplets and cooling the droplets for solidification. More specifically, the particles can be produced by carrying out the steps (1) to (4) shown below, for example.

Step (1): Add agar, a cyclodextrin and/or a plant protein, and optionally a silicate if desired to water, and mix them with heating for dissolution or dispersion to prepare an aqueous phase.

Step (2): Keeping the aqueous phase prepared in the above (1) at a temperature not allowing the agar to gelate (70 to 90° C.), add a carotenoid as an oily phase thereto, and agitate the mixture for homogeneous dispersion of the oily phase in the aqueous phase to give an oil-in-water emulsion composition.

Step (3): Allow the oil-in-water emulsion composition prepared in the above (2) to form droplets using a method known per se, such as the instillation method, the spraying method, and the dispersion method, and cool the droplets to give fine particles in a frozen state.

Step (4): Recover the fine particles produced in the above (3) and dry the particles using a shelf circulation dryer, a fluid-bed dryer, a vacuum freeze dryer, a vibration vacuum dryer, or the like until a desired moisture content is achieved to give particles having a structure in which a carotenoid is dispersed in an agar gel.

The composition of the aqueous phase prepared in the above step (1) varies depending on the desired degree of the exudation preventing effect or the like, and for example, the agar content is 20 to 40 parts by mass, the total content of the cyclodextrin and/or the plant protein is 5 to 30 parts by mass, and the water content is 200 to 500 parts by mass. In the cases where a silicate is added as desired, the amount is, for example, 1 to 10 parts by mass.

The ratio of the aqueous phase and the oily phase in the oil-in-water emulsion composition prepared in the above step (2) varies with the purity of the carotenoid constituting the oily phase, etc., and for example, when an oil containing 25% by mass carotenoid is used as the oily phase, the ratio of aqueous phase/oily phase is 90/10 to 97/3, preferably 92/8 to 95/5. In the cases where the oil-in-water emulsion composition is prepared at such a ratio, the ratio of continuous phase/dispersed phase in the carotenoid-containing particles after dried in the step (4) is about 60/40 to 90/10.

For the agitation in the above step (2), a high-speed disperser/emulsifier, such as a TK Homo Mixer (made by Primix Corp.) and a Clearmix (made by M Technique Co., Ltd.) may be used. In preferred agitation conditions, the number of rotations is 3000 to 10000 rpm and the agitation duration is 5 to 60 minutes.

The formation of fine particles in the above step (3) is preferably carried out by the spraying method for better productivity, specifically by spraying droplets in a tower charged with liquid nitrogen. For the spraying, a pressurized spraying nozzle, a rotational spraying nozzle, a rotating disk, etc. may be used, for example, and preferably, a rotational spraying nozzle is used. In the cases where a rotational spraying nozzle is used, a preferable number of rotations is 200 to 2000 rpm, for example. The cooling temperature is preferably −196 to −15° C., and more preferably −120 to −20° C.

The drying in the above step (4) is preferably carried out using a fluid-bed drying, which allows rapid drying. In this case, to prevent adhesion of the particles to each other after drying, it is preferred to add a lubricant, such as calcium stearate and glycerine fatty acid ester, to the fine particles before drying, followed by mixing. The amount of the lubricant is usually 1 to 6% by mass relative to 100% by mass of the fine particles. The drying is usually continued until the moisture content is reduced to 10% by mass or less, preferably 5% by mass or less. After drying, to prevent the obtained carotenoid-containing particles from electrostatically or otherwise adhering or caking together, a fluidizer, such as fine silicon dioxide powder, may be added and mixed. The amount of the fluidizer is usually 0.1 to 4% by mass relative to 100% by mass of the carotenoid-containing particles.

The average particle diameter of the carotenoid-containing particles obtained through the above steps is preferably 150 to 1000 μm, and more preferably 150 to 400 μm. Examples of the method for measuring the average particle diameter include laser diffractometry method, wet image analysis method, centrifugal sedimentation method, electrical sensing zone method, screening method, etc.

Examples of the apparatus for measuring the average particle diameter include a laser diffraction-based particle diameter distribution measuring apparatus, a laser diffraction-based particle size distribution measuring apparatus, a sprayed particle diameter distribution measuring apparatus, an image analysis-based particle diameter distribution measuring apparatus, a sound wave vibration-based screening apparatus, a centrifugal sedimentation-based particle diameter distribution measuring apparatus, a high precision particle diameter distribution measuring apparatus, a precision particle diameter distribution measuring apparatus, etc.

Any other components may be contained in the carotenoid-containing particles of the present invention as long as they do not inhibit the effect of the present invention. Examples of such components include an antioxidant, a pH adjuster, an emulsifier, a sweetener, a flavor, etc. These components may be added to either one of the aqueous phase and the oily phase depending on the nature.

Examples of the antioxidant include vitamin E, ascorbic acid, catechin, rosemary extract, sunflower extract, enzymatically modified rutin, ferulic acid, quercetin, etc. Examples of the pH adjuster include sodium hydroxide, sodium hydrogencarbonate, etc. Examples of the emulsifier include glycerine fatty acid ester, sorbitan fatty acid ester, sucrose fatty acid ester, polyoxyethylene sorbitan fatty acid ester, ascorbyl palmitate, lecithin, etc. Examples of the sweetener include acesulfame potassium, aspartame, neotame, etc. Examples of the flavor include plant essential oils, such as essential oils from citruses, such as orange, lemon, lime, grapefruit, etc., flower essential oils, peppermint oil, spearmint oil, and spice oils, oily extracts, such as Kola-nut extract, coffee extract, vanilla extract, cocoa extract, tea extract, spice extract, etc., oleoresins thereof, synthetic flavor compounds (for example, L-menthol etc.), oily prepared flavor compositions, oily flavors as a mixture of these in any combination, powder flavors obtained by drying with any excipient, etc.

The carotenoid-containing particles of the present invention can preferably be used as a food material having a color of carotenoid (yellow to red or the like) or as an ingredient having physiological activities, such as a provitamin A activity, an antioxidant action, and an anticancer/antitumor action, in foods, drugs, health foods, or the like. Alternatively, the carotenoid-containing particles of the present invention may be used as foods, health foods, drugs, or the like as they are.

In the cases where the carotenoid-containing particles of the present invention are blended in foods or health foods, the form of the foods or health foods is not particularly limited. For example, the particles may be blended in confectioneries, such as baked confectioneries, chocolates, chewing gums, hard candies, and gummy candies; desserts, such as yogurt, ice cream, and pudding; or tablet candies (including supplement tablets) produced by tableting using an excipient or the like in the form of a powder.

In the cases where the carotenoid-containing particles of the present invention are blended in drugs, the form of the drugs is not particularly limited. With appropriately blended pharmaceutical additives, food additives, food materials, etc., the carotenoid-containing particles of the present invention may be formed into a formulation, such as a powder, a granule, a tablet, a microcapsule, a soft capsule, a hard capsule, or the like by a conventional method.

In particular, since the carotenoid-containing particles of the present invention, as compared with conventional carotenoid-containing particles not containing gelatin in the continuous phase, are less likely to cause exudation of carotenoid even when tableting pressure is applied, preferred is that the particles are blended in tablet candies or tablets among the above-mentioned forms of foods, health foods, and drugs.

In the cases where the carotenoid-containing particles of the present invention are blended in tablet candies or tablets, the method for producing the tablet candies or tablets is not particularly limited. For example, such tablet candies or tablets can be produced by blending the particles of the present invention with an excipient, a binder, a disintegrant, a lubricant, a fluidizer, a colorant, a flavor, a sweetener, etc., followed by tableting by a method known per se.

Examples of the excipient include cellulosic substances, such as crystalline cellulose; sugars, such as lactose and purified sucrose; sugar alcohols, such as D-sorbitol, D-mannitol, erythritol, and trehalose; starches, such as corn starch, potato starch, and partly pregelatinized starch; and inorganic substances, such as calcium phosphate, anhydrous dibasic calcium phosphate, aluminium silicate, and magnesium aluminometasilicate. Examples of the binder include cellulose derivatives, such as hydroxypropylcellulose, hydroxypropylmethylcellulose, carmellose sodium, and methyl cellulose, synthetic polymers, such as polyvinyl pyrrolidone. Examples of the disintegrant include cellulosic derivatives, such as carmellose calcium, low substituted hydroxypropylcellulose, and croscarmellose sodium; and starches and starch derivatives, such as corn starch, sodium starch glycolate, hydroxypropyl starch, and partly pregelatinized starch. Examples of the lubricant include magnesium stearate, calcium stearate, amorphous silicon oxide hydrate, magnesium silicate, calcium silicate, magnesium carbonate, sucrose fatty acid ester, and polyglyceryl fatty acid ester. Examples of the fluidizer include light anhydrous silicic acid, silicon dioxide, titanium oxide, and talc.

The carotenoid-containing particles of the present invention are characterized in that the exudation of carotenoid at the time of tableting and during storage is prevented, and therefore, even when the carotenoid content in the particles is increased, exudation of carotenoid is less likely to occur. For that reason, by using the carotenoid-containing particles of the present invention prepared so as to contain an increased amount of carotenoid as compared with conventional carotenoid-containing particles, efficient carotenoid intake can be achieved.

The carotenoid-containing particles of the present invention are not necessarily free from materials of animal origin, such as gelatin, but can be produced so as not to contain any material of animal origin. Therefore, the carotenoid-containing particles of the present invention can be produced as a product with reduced risk of inducing allergy attributable to a material of animal origin, if desired.

Hereinafter, the present invention will be illustrated in more detail by Examples, but the present invention is not limited thereto.

EXAMPLES

Experimental Example 1

Production of Various Carotenoid-Containing Particles (1) Ingredients
1) α-Cyclodextrin (trade name: Dexy pearl α-100; made by Ensuiko Sugar Refining Co., Ltd.)
2) β-Cyclodextrin (trade name: Dexy pearl β-100; made by Ensuiko Sugar Refining Co., Ltd.)
3) γ-Cyclodextrin (trade name: Dexy pearl γ-100; made by Ensuiko Sugar Refining Co., Ltd.)
4) Soy protein (trade name: Fujipro FX; made by Fuji Oil Co., Ltd.)
5) Green pea protein (trade name: Protein GP; made by Daiichi Kasei Co., Ltd.)
6) Rice protein (trade name: Oryza Protein-P70; made by Oryza Oil & Fat Chemical Co., Ltd.)
7) Agar (trade name: Ina Agar UP-37; made by Ina Food Industry)
8) Granulated sugar (trade name: Granulated Sugar GN; made by Mitsui Sugar Co., Ltd.)
9) Antioxidant (L-ascorbyl palmitate; trade name: Grindox ascorbyl palmitate; made by Danisco)
10) pH adjuster (sodium hydroxide; trade name: Tosoh Pearl; made by Tosoh Corp.)
11) Astaxanthin (trade name: AstaReal Oil 50F; oil containing 5% by mass astaxanthin; made by Fuji Chemical Industries Co., Ltd.)
12) Lutein (trade name: FloraGLO Lutein 20% suspension SAF; oil containing 20% by mass lutein; made by DSM)
13) β-Caroten (trade name: Lucarotin 30M; oil containing 30% by mass β-caroten; made by BASF)

(2) Compositions of Carotenoid-Containing Particles

The compositions of various carotenoid-containing particles produced using the above-described ingredients are shown in Table 1. Carotenoid-containing particles 1 to 7 are examples of the present invention, and Carotenoid-containing particles 8 to 10 are comparative examples for comparison therewith.

(3) Method for Producing Carotenoid-Containing Particles

To an aluminum jug having a capacity of 1 L, 400 g of tap water was added, and warmed to 85° C. To this, in accordance with the blended amounts shown in Table 1, all the ingredients except the carotenoid (astaxanthin, lutein, or β-carotene) were added, and stirred and mixed with a TK Homo Mixer (trade name; Type: MARK 2.5; made by Primix Corp.) at 4000 rpm for 10 minutes to give a homogeneous solution or dispersion, which was used as an aqueous phase.

While the aqueous phase was kept at 85° C., the carotenoid as an oily phase was added thereto, and stirred with a TK Homo Mixer at 10000 rpm for 10 minutes for homogeneous dispersion of the oily phase in the aqueous phase to give an oil-in-water emulsion composition.

Subsequently, the oil-in-water emulsion composition was fed to a spray cooling apparatus (testing machine) of which the lower part of the tower was cooled with liquid nitrogen, and sprayed in the form of spheres from a rotational spraying nozzle rotating at 1200 rpm. The sprayed composition was cooled to drop to the lower part of the tower, and was recovered in the form of frozen particles.

To 400 g of the recovered particles, 4 g of calcium stearate (made by Sun Ace Corp.) was added and mixed for preventing the particles from adhering to each other. Then, the particles were dried using a fluid-bed dryer (Type: LAB-1; made by Powrex Corp.) at 20° C. for 30 minutes, at 30° C. for 1 hour, and at 60° C. for 30 minutes in this order. To the dried particles, 0.2 g of fine silicon dioxide powder (trade name: Carplex FPS-500; made by Evonik Industries) was added and mixed to prevent the particles from electrostatically or otherwise adhering or caking together. The particles were sieved with a No. 26 screen (opening: 600 μm), and particles having passed through the sieve were recovered. In this manner, 70 g each of Carotenoid-containing particles 1 to 10 were obtained. The carotenoid-containing particles were red or brown in color depending on the color of the carotenoid used as an ingredient (astaxanthin and β-carotene: red, lutein: brown).

The moisture content and the average particle diameter of the Carotenoid-containing particles 1 were determined to be about 3.0% by mass and about 300 μm, respectively.

TABLE 1

| | Blended amount (g) | | | | | | | | | |
|---|---|---|---|---|---|---|---|---|---|---|
| | Carotenoid-containing particles | | | | | | | | | |
| Ingredient | 1 | 2 | 3 | 4 | 5 | 6 | 7 | 8 | 9 | 10 |
| α-Cyclodextrin | 10 | — | — | — | — | — | — | — | — | — |
| β-Cyclodextrin | — | 10 | — | — | 5 | 5 | — | — | — | — |
| γ-Cyclodextrin | — | — | 10 | — | — | — | 15 | — | — | — |
| Soy protein | — | — | — | 15 | — | 5 | — | — | — | — |
| Green pea protein | — | — | — | — | 15 | — | — | — | — | — |
| Rice protein | — | — | — | — | — | — | 10 | — | — | — |
| Agar | 20 | 20 | 30 | 20 | 20 | 20 | 25 | 20 | 40 | 30 |
| Granulated sugar | 37.60 | 49.20 | 42.60 | 43.65 | 28.65 | 49.20 | 7.60 | 67.60 | 47.60 | 50.42 |
| Antioxidant | 3.0 | 1.5 | 3.0 | 2.0 | 2.0 | 1.5 | 3.0 | 3.0 | 3.0 | 5.0 |
| pH adjuster | 0.2 | 0.1 | 0.2 | 0.2 | 0.2 | 0.1 | 0.2 | 0.2 | 0.2 | 0.38 |
| Carotenoid Astaxanthin | 25 | — | — | — | 25 | — | — | 5 | 5 | — |
| Lutein | — | 15 | — | — | — | 15 | 35 | — | — | — |
| β-Caroten | — | — | 10 | 15 | — | — | — | — | — | 10 |

Evaluation Test of Exudation of Carotenoid Immediately After Production and After Storage Each of the Carotenoid-containing particles 1 to 10 in an amount of 10 g were weighed out and placed on a filter paper (70 mm in diameter; made by Advantec Co., Ltd.) in a petri dish (80 mm in diameter, 15 mm in depth; made by As One Corp.), and stored in an incubator set at 40° C. The condition of the filter paper was visually examined before the storage (immediately after production), after 1-month storage, and after 2-month storage. In a case where color transfer (i.e., red or brown coloration) was observed in a part in contact with the carotenoid-containing particles, the exudation of carotenoid was judged to be "+ (plus)", and in a case where such color transfer was not observed, the exudation of carotenoid was judged to be "− (minus)". The results are shown in Table 2.

TABLE 2

|  | Carotenoid-containing particles | Exudation of carotenoid | | |
|---|---|---|---|---|
|  |  | Before storage | After storage (40° C., 1 month) | After storage (40° C., 2 months) |
| Examples | 1 | − | − | − |
|  | 2 | − | − | − |
|  | 3 | − | − | − |
|  | 4 | − | − | − |
|  | 5 | − | − | − |
|  | 6 | − | − | − |
|  | 7 | − | − | − |
| Comparative Examples | 8 | + | + | + |
|  | 9 | − | + | + |
|  | 10 | − | + | + |

As the results in Table 2 clearly show, in the cases of the Carotenoid-containing particles 1 to 7 as examples of the present invention, color transfer to the filter paper was not observed even after 2-month storage, meaning that exudation of carotenoid from the particles during storage was prevented. In contrast, in the cases of the Carotenoid-containing particles 8 to 10 as comparative examples, exudation of carotenoid from the particles occurred during storage. In particular, the Carotenoid-containing particles 8 already showed exudation of carotenoid before storage (immediately after production), obviously demonstrating an insufficient exudation preventing effect.

Evaluation Test of Exudation of Carotenoid Due to Tableting
(1) Method for Producing Tablets A raw material powder was obtained by mixing 0.5 g of one of the Carotenoid-containing particles 1 to 10, 9.4 g of D-sorbitol granules (trade name: Sorbitol TBS; made by B Food Science Co., Ltd.), and 0.1 g of a sucrose fatty acid ester (trade name: DK Ester F-20W; made by DKS Co., Ltd.). Each raw material powder was charged into a die 18 mm in diameter, and compressed with a pressure of 2 tons per tablet using a single punch tableting machine (Type: High Pressure Jack J-1; made by As One Corp.) to give Tablets 1 to 10. For each kind of Tablets 1 to 10, 10 tablets (1 g per tablet) were produced. The appearance of the tablets was such that red or brown spots are on a white background because the tablets contained red or brown carotenoid-containing particles scattered in a white base.

The obtained Tablets 1 to 10 (5 tablets per kind) were separately put in polyethylene bags and further put in aluminum laminated bags (PET/AL/PE) for higher light blocking effect and airtightness, and stored in an incubator set at 40° C. The remaining 5 tablets were also put in the bags as above for higher light blocking effect and airtightness, and stored in a refrigerator at 5° C. to avoid time-dependent exudation of carotenoid. These 5 tablets were used as a comparison standard appearing almost the same as immediately after tableting (see FIGS. 2 to 11).

(2) Evaluation of Exudation of Carotenoid by Visual Examination

Immediately after tableting, after storage at 40° C. for 10 days, and after storage at 40° C. for 20 days, one tablet of each of the Tablets 1 to 10 was taken in a random manner and the surface was visually observed. Based on the size of the spots seen on the surface due to the color of the carotenoid-containing particles, the condition of exudation of carotenoid was evaluated. The evaluation was based on the following criteria. The results are shown in Table 3.

Criteria

Excellent: Spots are extremely minute.
Good: A few larger spots exist but spots are generally minute.
Poor: Larger spots are conspicuous.

(3) Determination of Standard Diameter of Spots

For quantitatively evaluating the condition of exudation of carotenoid from the Tablets 1 to 10, the standard diameter of spots was determined immediately after tableting, after storage at 40° C. for 10 days, and after storage at 40° C. for 20 days, by the method shown below. The results are shown in Table 3.

The standard diameter can be smaller than the average particle diameter of the carotenoid-containing particles immediately after production (about 300 μm) for the reason that the carotenoid-containing particles are compacted by the pressure of tableting and that the particles can only partly appear on the tablet surface.

Method for Determining Standard Diameter of Spots

Using a microscope (Type: VHX-500F; made by Keyence Corp.), a tablet is observed at a magnification of 100 times, and the diameters of 5 relatively large spots among spots seen on the surface due to the color of the carotenoid-containing particles are measured. The average (rounded to the nearest whole number) of the 5 diameters is regarded as the standard diameter of spots.

TABLE 3

|  | Tablet | Carotenoid-containing particles | Immediately after tableting | | After storage (40° C., 10 days) | | After storage (40° C., 20 days) | |
|---|---|---|---|---|---|---|---|---|
|  |  |  | Visual evaluation | Standard diameter of spots | Visual evaluation | Standard diameter of spots | Visual evaluation | Standard diameter of spots |
| Examples | 1 | 1 | Excellent | 150 μm | Excellent | 165 μm | Good | 195 μm |
|  | 2 | 2 | Excellent | 165 μm | Excellent | 170 μm | Good | 195 μm |
|  | 3 | 3 | Excellent | 155 μm | Excellent | 170 μm | Good | 190 μm |
|  | 4 | 4 | Excellent | 170 μm | Excellent | 185 μm | Good | 200 μm |
|  | 5 | 5 | Excellent | 165 μm | Excellent | 170 μm | Excellent | 170 μm |

TABLE 3-continued

|  | Tablet | Carotenoid-containing particles | Immediately after tableting | | After storage (40° C., 10 days) | | After storage (40° C., 20 days) | |
|---|---|---|---|---|---|---|---|---|
|  |  |  | Visual evaluation | Standard diameter of spots | Visual evaluation | Standard diameter of spots | Visual evaluation | Standard diameter of spots |
|  | 6 | 6 | Excellent | 160 μm | Excellent | 165 μm | Excellent | 165 μm |
|  | 7 | 7 | Excellent | 170 μm | Excellent | 170 μm | Excellent | 170 μm |
| Comparative | 8 | 8 | Poor | 320 μm | Poor | 480 μm | Poor | 535 μm |
| Examples | 9 | 9 | Good | 215 μm | Poor | 320 μm | Poor | 395 μm |
|  | 10 | 10 | Poor | 340 μm | Poor | 470 μm | Poor | 520 μm |

As the results in Table 3 clearly show, regarding the Tablets 1 to 7 containing the Carotenoid-containing particles 1 to 7 as examples of the present invention, at any time point of immediately after tableting, after 10-day storage, and after 20-day storage, the visually evaluated condition of exudation of carotenoid was excellent or good, and the standard diameter of the spots was equal to or less than the average particle diameter of the carotenoid-containing particles immediately after production. In particular, regarding the Tablets 5 to 7 containing the Carotenoid-containing particles 5 to 7 in which both a cyclodextrin and a plant protein were used, the standard diameter of the spots even after 20-day storage was almost the same as that immediately after tableting, demonstrating an outstanding preventing effect on the exudation of carotenoid.

In contrast, regarding the Tablets 8 to 10 containing the Carotenoid-containing particles 8 to 10 as comparative examples, exudation of carotenoid occurred at least after 10-day storage. In particular, regarding the Tablets 8 and 10, visually observable exudation of carotenoid already occurred immediately after tableting, revealing lack of strength withstanding the tableting pressure (see FIGS. 9 and 11).

Experimental Example 2

Production of Carotenoid-Containing Particles (Having High Content of Astaxanthin)

(1) Ingredients
1) β-Cyclodextrin (trade name: Dexy pearl β-100; made by Ensuiko Sugar Refining Co., Ltd.)
2) Green pea protein (trade name: Protein GP; made by Daiichi Kasei Co., Ltd.)
3) Calcium silicate (trade name: Florite R; made by Tomita Pharmaceutical Co., Ltd.)
4) Agar (trade name: Ina Agar UP-37; made by Ina Food Industry)
5) Granulated sugar (trade name: Granulated Sugar GN; made by Mitsui Sugar Co., Ltd.)
6) Antioxidant (L-ascorbyl palmitate; trade name: Grindox ascorbyl palmitate; made by Danisco)
7) pH adjuster (sodium hydroxide; trade name: Tosoh Pearl; made by Tosoh Corp.)
8) Astaxanthin (trade name: AstaReal Oil 50F; oil containing 5% by mass astaxanthin; made by Fuji Chemical Industries Co., Ltd.)

(2) Compositions of Carotenoid-Containing Particles
The compositions of Carotenoid-containing particles 11 to 13 produced using the above-described ingredients are shown in Table 4. The Carotenoid-containing particles 11 to 13 are examples of the present invention, wherein the astaxanthin content is increased as compared with the Carotenoid-containing particles 1 and 5 in the above Experimental Example 1.

TABLE 4

| Ingredient | Blended amount (g) Carotenoid-containing particles | | |
|---|---|---|---|
|  | 11 | 12 | 13 |
| β-Cyclodextrin | 10 | 10 | 10 |
| Green pea protein | 15 | 15 | 15 |
| Calcium silicate | — | 2 | 6 |
| Agar | 20 | 20 | 20 |
| Granulated sugar | 7.60 | 5.60 | 1.60 |
| Antioxidant | 3.0 | 3.0 | 3.0 |
| pH adjuster | 0.2 | 0.2 | 0.2 |
| Astaxanthin | 40 | 40 | 40 |

(3) Method for Producing Carotenoid-Containing Particles

To an aluminum jug having a capacity of 1 L, 400 g of tap water was added, and warmed to 85° C. To this, in accordance with the blended amounts shown in Table 4, all the ingredients except the carotenoid (astaxanthin) were added, and stirred and mixed with a TK Homo Mixer (trade name; Type: MARK 2.5; made by Primix Corp.) at 4000 rpm for 10 minutes to give a homogeneous solution or dispersion, which was used as an aqueous phase.

While the aqueous phase was kept at 85° C., astaxanthin as an oily phase was added thereto, and stirred with a TK Homo Mixer at 10000 rpm for 10 minutes for homogeneous dispersion of the oily phase in the aqueous phase to give an oil-in-water emulsion composition.

Subsequently, the oil-in-water emulsion composition was fed to a spray cooling apparatus (testing machine) of which the lower part of the tower was cooled with liquid nitrogen, and sprayed in the form of spheres from a rotational spraying nozzle rotating at 1200 rpm. The sprayed composition was cooled to drop to the lower part of the tower, and was recovered in the form of frozen particles.

To 400 g of the recovered particles, 4 g of calcium stearate (made by Sun Ace Corp.) was added and mixed for preventing the particles from adhering to each other. Then, the particles were dried using a fluid-bed dryer (Type: LAB-1; made by Powrex Corp.) at 20° C. for 30 minutes, at 30° C. for 1 hour, and at 60° C. for 30 minutes in this order. To the dried particles, 0.2 g of fine silicon dioxide powder (trade name: Carplex FPS-500; made by Evonik Industries) was added and mixed to prevent the particles from electrostatically or otherwise adhering or caking together. The particles were sieved with a No. 26 screen (opening: 600 μm), and particles having passed through the sieve were recovered. In this manner, 70 g each of the Carotenoid-containing particles 11 to 13 were obtained. The carotenoid-containing particles were red, which was the color of the astaxanthin used as an ingredient.

The moisture content and the average particle diameter of the Carotenoid-containing particles 11 were determined to be about 3.0% by mass and about 300 μm, respectively.

Evaluation Test of Exudation of Carotenoid Due to Tableting

TABLE 5

|  | Tablet | Carotenoid-containing particles | Immediately after tableting | | After storage (40° C., 5 days) | |
|---|---|---|---|---|---|---|
|  |  |  | Visual evaluation | Standard diameter of spots | Visual evaluation | Standard diameter of spots |
| Examples | 11 | 11 | Excellent | 160 μm | Good | 195 μm |
|  | 12 | 12 | Excellent | 155 μm | Excellent | 165 μm |
|  | 13 | 13 | Excellent | 155 μm | Excellent | 155 μm |

(1) Method for Producing Tablets

A raw material powder was obtained by mixing 0.5 g of one of the Carotenoid-containing particles 11 to 13, 9.4 g of D-sorbitol granules (trade name: Sorbitol TBS; made by B Food Science Co., Ltd.), and 0.1 g of a sucrose fatty acid ester (trade name: DK Ester F-20W; made by DKS Co., Ltd.). Each raw material powder was charged into a die 18 mm in diameter, and compressed with a pressure of 2 tons per tablet using a single punch tableting machine (Type: High Pressure Jack J-1; made by As One Corp.) to give Tablets 11 to 13. For each kind of Tablets 11 to 13, 10 tablets (1 g per tablet) were produced. The appearance of the tablets was such that red spots are on a white background because the tablets contained red carotenoid-containing particles scattered in a white base.

The obtained Tablets 11 to 13 were separately put in polyethylene bags and further put in aluminum laminated bags (PET/AL/PE) for higher light blocking effect and airtightness, and stored in an incubator set at 40° C.

(2) Evaluation of Exudation of Carotenoid by Visual Examination

Immediately after tableting and after storage at 40° C. for 5 days, one tablet of each of Tablets 11 to 13 was taken in a random manner and the surface was visually observed. Based on the size of the spots seen on the surface due to the color of the carotenoid-containing particles, the condition of exudation of carotenoid was evaluated. The evaluation was based on the following criteria. The test results are shown in Table 5.

Criteria

Excellent: Spots are extremely minute.
Good: A few larger spots exist but spots are generally minute.
Poor: Larger spots are conspicuous.

(3) Determination of Standard Diameter of Spots

For quantitatively evaluating the condition of exudation of carotenoid from the Tablets 11 to 13, the standard diameter of spots was determined immediately after tableting and after storage at 40° C. for 5 days, by the method shown below. The results are shown in Table 5.

The standard diameter can be smaller than the average particle diameter of the carotenoid-containing particles immediately after production (about 300 μm) for the reason that the carotenoid-containing particles are compacted by the pressure of tableting and that the particles can only partly appear on the tablet surface.

Method for Determining Standard Diameter of Spots

Using a microscope (Type: VHX-500F; made by Keyence Corp.), a tablet is observed at a magnification of 100 times, and the diameters of 5 relatively large spots among spots seen on the surface due to the color of the carotenoid-containing particles are measured. The average (rounded to the nearest whole number) of the 5 diameters is regarded as the standard diameter of spots.

As the results in Table 5 clearly show, regarding the Tablets 11 to 13 containing the Carotenoid-containing particles 11 to 13 as examples of the present invention, even in the cases where relatively large amount of astaxanthin was contained in the carotenoid-containing particles, the visual evaluation was excellent or good, and the standard diameter of the spots was equal to or less than the average particle diameter of immediately after production. In particular, regarding the Tablets 12 and 13 containing the Carotenoid-containing particles 12 and 13 containing calcium silicate, the standard diameter of the spots even after 5-day storage was almost the same as that immediately after tableting, demonstrating an outstanding preventing effect on the exudation of carotenoid.

REFERENCE SIGNS LIST

1 Continuous phase (agar gel containing cyclodextrin and/or plant protein)
2 Dispersed phase (carotenoid)

The invention claimed is:

1. Carotenoid-containing particles comprising a structure in which a carotenoid is dispersed in an agar gel comprising a plant protein,
   wherein said agar has a jelly strength of 250 to 350 g/cm$^2$ as measured by the Nikkansui method,
   wherein the agar content in the particles is 20 to 40 parts by mass, and the content in the particles of the plant protein is 5 to 15 parts by mass,
   wherein said plant protein comprises soybean protein, wheat protein, rice protein, green pea protein, corn protein, or any combination thereof, and
   wherein the exudation of carotenoid at the time of tableting or during storage is prevented when the particles are blended into tablet candies or tablets.

2. A method for producing carotenoid-containing particles comprising a structure in which a carotenoid is dispersed in an agar gel comprising a plant protein or a cyclodextrin, the method comprising:
   preparing an oil-in-water emulsion composition by dispersing an oily phase comprising a carotenoid in an aqueous phase comprising an agar and a cyclodextrin or a plant protein;
   subsequently, allowing the oil-in-water emulsion composition to form droplets; and cooling the droplets until solidified,
   wherein said agar has a jelly strength of 250 to 350 g/cm$^2$ as measured by the Nikkansui method,
   wherein the agar content in the particles is 20 to 40 parts by mass, and the content in the particles of the plant protein or cyclodextrin is 5 to 15 parts by mass, wherein said plant protein comprises soybean protein, wheat protein, rice protein, green pea protein, corn protein, or any combination thereof, wherein said cyclodextrin comprises α-cyclodextrin, β-cyclodextrin, γ-cyclodextrin, or any combination thereof, and wherein the exudation of carotenoid at the time of tableting or during storage is prevented when the particles are blended into tablet candies or tablets.

3. The carotenoid-containing particles of claim 1, wherein said agar is prepared from a *Gelidium, Gracilaria, Pterocladiella*, or *Ahnfeltia* species.

4. The carotenoid-containing particles of claim 1, wherein said agar has an average molecular weight of 50000-60000 as determined by gel filtration chromatography.

5. The carotenoid-containing particles of claim 1, wherein said carotenoid-containing particles comprise an aqueous phase and an oily phase.

6. The carotenoid-containing particles of claim 1, further comprising a silicate.

7. The carotenoid-containing particles of claim 6, wherein the silicate comprises an alkaline earth metal silicate.

8. The carotenoid-containing particles of claim 7, wherein the alkaline earth metal silicate comprises a calcium silicate, a magnesium silicate, a magnesium trisilicate, an aluminum silicate, a calcium aluminum silicate, a calcium magnesium silicate, a calcium magnesium orthosilicate or an aluminum magnesium silicate.

9. The carotenoid-containing particles of claim 1, wherein the carotenoid comprises β-carotene, α-carotene, γ-carotene, β-apo-8'-carotenal, β-apo-10'-carotenal, β-apo-8'-carotenic acid, citranaxanthin, lycopene, zeaxanthin, cryptoxanthin, echinenone, 3-hydroxy-β-carotene, fucoxanthin, lutein, astaxanthin, canthaxanthin, capsanthin, capsorubin, bixin, crocetin, or esters of a hydroxyl- or carboxyl-group-containing compound thereof.

10. The carotenoid-containing particles of claim 1, wherein the particle size of the carotenoid-containing particles is 150-1000 μm.

11. The carotenoid-containing particles of claim 1, wherein the particle size of the carotenoid-containing particles is 150-400 μm.

12. The carotenoid-containing particles of claim 1, further comprising an antioxidant, a pH adjuster, an emulsifier, a sweetener, or a flavor.

13. The carotenoid-containing particles of claim 12, wherein said antioxidant, a pH adjuster, an emulsifier, a sweetener, or a flavor is incorporated into an aqueous phase.

14. The carotenoid-containing particles of claim 12, wherein said antioxidant, a pH adjuster, an emulsifier, a sweetener, or a flavor is incorporated into an oily phase.

15. The carotenoid-containing particles of claim 12, wherein said antioxidant is vitamin E, ascorbic acid, catechin, rosemary extract, sunflower extract, enzymatically modified rutin, ferulic acid, or quercetin.

16. The carotenoid-containing particles of claim 12, wherein said pH adjuster comprises sodium hydroxide or sodium hydrogencarbonate.

17. The carotenoid-containing particles of claim 12, wherein said emulsifier comprises glycerine fatty acid ester, sorbitan fatty acid ester, sucrose fatty acid ester, polyoxyethylene sorbitan fatty acid ester, ascorbyl palmitate or lecithin.

18. The carotenoid-containing particles of claim 1, wherein the agar gel further comprises a cyclodextrin.

19. Carotenoid-containing particles comprising a structure in which a carotenoid is dispersed in an agar gel comprising a cyclodextrin, wherein said agar has a jelly strength of 250 to 350 g/cm$^2$ as measured by the Nikkansui method, wherein the agar content in the particles is 20 to 40 parts by mass, and the content in the particles of the cyclodextrin is 5 to 15 parts by mass, wherein said cyclodextrin comprises α-cyclodextrin, β-cyclodextrin, γ-cyclodextrin, or any combination thereof, and wherein the exudation of carotenoid at the time of tableting or during storage is prevented when the particles are blended into tablet candies or tablets.

\* \* \* \* \*